(12) United States Patent
Castro

(10) Patent No.: US 12,016,599 B2
(45) Date of Patent: Jun. 25, 2024

(54) LONG BONE FRACTURE REDUCTION SYSTEM

(71) Applicant: Frank Castro, Louisville, KY (US)

(72) Inventor: Frank Castro, Louisville, KY (US)

(73) Assignee: MEDICAL PATENTS LLC, Nicholasville, KY (US)

( * ) Notice: Subject to any disclaimer, the term of this patent is extended or adjusted under 35 U.S.C. 154(b) by 1141 days.

(21) Appl. No.: 16/646,596

(22) PCT Filed: Jul. 9, 2019

(86) PCT No.: PCT/US2019/040923
§ 371 (c)(1),
(2) Date: Mar. 12, 2020

(87) PCT Pub. No.: WO2020/076383
PCT Pub. Date: Apr. 16, 2020

(65) Prior Publication Data
US 2021/0212736 A1    Jul. 15, 2021

Related U.S. Application Data

(60) Provisional application No. 62/743,457, filed on Oct. 9, 2018.

(51) Int. Cl.
*A61B 17/72* (2006.01)
(52) U.S. Cl.
CPC .................... *A61B 17/7275* (2013.01)
(58) Field of Classification Search
CPC ............ A61B 17/7275; A61B 17/7098; A61B 17/7233; A61B 17/8897; A61B 17/7225

USPC ...................................................... 606/62–68
See application file for complete search history.

(56) References Cited

U.S. PATENT DOCUMENTS

| 8,128,626 | B2 | 3/2012 | Justin |
| 8,715,284 | B2 | 5/2014 | Culbert |
| 9,283,006 | B2 | 3/2016 | Fonte |
| 2002/0032444 | A1 | 3/2002 | Mische |
| 2007/0173939 | A1* | 7/2007 | Kim ............ A61B 17/8858 623/17.11 |
| 2008/0255559 | A1 | 10/2008 | Leyden et al. |
| 2009/0005782 | A1* | 1/2009 | Chirico ......... A61B 17/8811 606/300 |
| 2009/0143781 | A1 | 6/2009 | Mische |
| 2010/0286692 | A1 | 11/2010 | Greenhalgh et al. |
| 2011/0004255 | A1 | 1/2011 | Weiner et al. |
| 2012/0065638 | A1 | 3/2012 | Moore |
| 2012/0184999 | A1 | 7/2012 | Khanna |
| 2013/0072933 | A1 | 3/2013 | Bidermann et al. |
| 2013/0296861 | A1 | 11/2013 | Tonz |
| 2015/0223849 | A1 | 8/2015 | McCormick et al. |
| 2017/0290614 | A1 | 10/2017 | Weiner et al. |

FOREIGN PATENT DOCUMENTS

EP   1582161    10/2005
WO   2008109566  9/2008

* cited by examiner

*Primary Examiner* — Eduardo C Robert
*Assistant Examiner* — Tara Rose E Carter
(74) *Attorney, Agent, or Firm* — BUSINESS PATENT LAW, PLLC

(57) ABSTRACT

The present invention is a system or implant adapted for use in bone cavities. The current system is particularly useful in surgical procedures involving fractured bones.

19 Claims, 5 Drawing Sheets

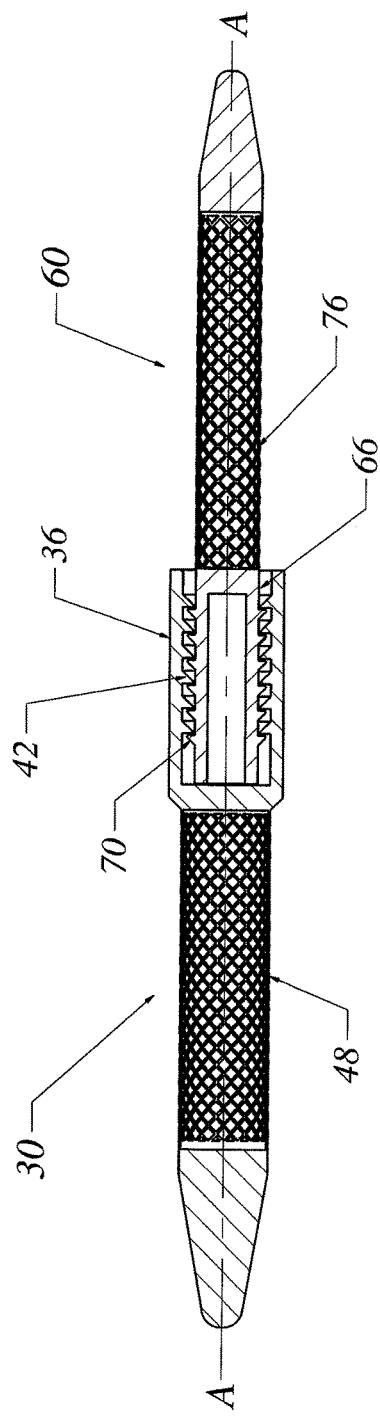
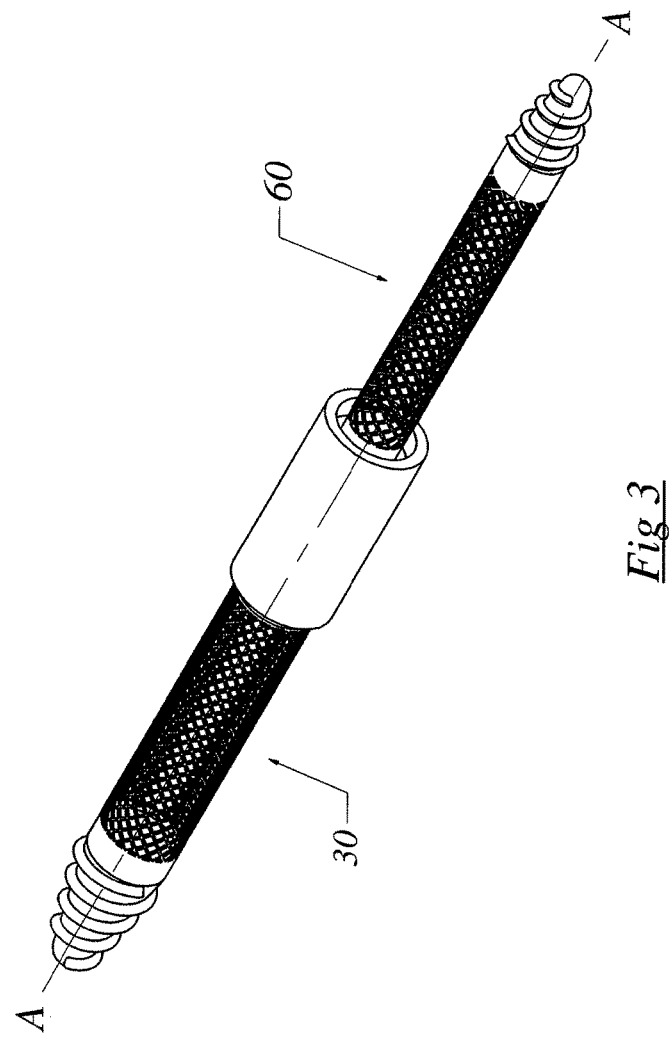
Fig 2
Fig 3

LONG BONE FRACTURE REDUCTION SYSTEM

PRIORITY

Applicant claims priority to PCT/US2019/040923—Long Bone Fracture Reduction System—, filed Jul. 9, 2019 that claims the benefit of U.S. Provisional Application No. 62/743,457—Long Bone Fracture Reduction System—filed on Oct. 9, 2018.

BACKGROUND OF THE INVENTION

A. Field of the Invention

Among other things, the present invention is a system, combination or implant that has interlocking first and second devices or components. The current system is useful in the treatment of mammalian bone fractures. Meshes can be attached to or integral with the first and second components.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references. References that may indicate a state-of-the-art for the current invention include: 1) US Published Patent Application 20020032444-Mische; 2) US Published Patent Application 20110004255-Weiner, et al.; 3) US Published Patent Application No. 20090143781-Mische; 4) U.S. Pat. No. 8,715,284-Culbert; 5) US Published Patent Application 20080255559-Leyden, et al.; 6) U.S. Pat. No. 8,128,626-Justin; 7) U.S. Pat. No. 9,283,006-Fonte; and 8) US Published Patent Application 20120184999-Khanna.

Prior to the current invention, in minimally first line surgeries to repair a fractured long bone, surgeons would pass a guide wire through the proximal fractured side into the distal fractured side. Generally, a rod was also passed over the guide wire. Through the use of forces external to the outward surfaces of opposed fractured sides, the fractured sides were manipulated into positions that approximated their pre-fracture state. In the proximal and distal fractured sides, the rod was locked into place with screws. Locking the rod minimized the vertical, horizontal and rotational movement of the implant, and in many cases, such stabilization of the injured environment was sufficient for bone healing. However, there are many times when the first line prior art surgical methods failed to adequately anatomically realign the fractured sections and subsequent surgery was required to improve healing of the fractured bone. By way of illustration, due to resorption of bone or gaps caused bone loss from the injury, prior art first line surgeries were frequently inadequate to improve healing of the fracture.

SUMMARY OF THE INVENTION

The present invention provides a biocompatible implant or system that can be inserted into opposed cavities of fractured sides of bone. The current combination or implant can be provided with male and female components that have interlocking teeth to limit movements of the female and male components. Among other things, the male device is provided with a body and a channel and the female component is provided with a body and a conduit. Each interlocking component can also be supplied with an opening there through.

The system's male component and the female receptacle are provided with expandable meshes. The combination of the male and female devices and the meshes create a duct along a longitudinal axis of the implant. After implantation into a cavity or cortex of opposed sides of a fractured long bone, a mesh can be expanded to contact a healthy (unbroken) area of the wall surrounding the cavity. Among other things, the implant's expanded meshes hold the opposed sides of fractured bone and allow the opposed sides to be compressed against each other and to assist with the healing of the fracture.

It has been estimated that between five to ten percent of long bone fractures treated with prior art surgical implants, techniques and procedures fail to heal. Such postoperative conditions as bone resorption, improper alignment of the opposed sides of the fractured bone or low grade infection can precipitate a non-union of fracture fragments. When the long bone fracture fails to heal after utilizing prior art fixation systems, a second or third surgical procedure may be required to create a union between the fractured fragments. For example, when intramedullary rod fixation was used in the first surgical treatment, the implanted rod holds the fracture fragments and bone length constant by placing screws at opposite ends of the rod. Stabilizing the repaired bone's fractured sides to a constant length reduces the dynamic compression between the fractured sides. It is believed that dynamic compression enhances healing between the fractured sides of the broken bone.

When using the prior art's intramedullary rods, if postoperative non-union occurred, a first treatment option was to remove the distal screws to allow for dynamic compression or a second treatment option required a second surgery to remove the first implant rod and replace the first rod with a second larger rod. The second surgery's implantation of the second larger rod was typically more invasive than the first surgical procedure.

From the initial surgical procedure to repair the broken bone, use of the current invention allows for dynamic compression of the opposed broken sides of the fractured bone. It is believed that the dynamic compression provided by the present invention's system of interlockers reduces the risk of a second or third surgical procedure.

An aspect of the present invention is to provide a combination securing fractured ends of a broken bone; the combination comprising: a) a first device comprising: i) a first cylindrical body; ii) a female receptacle integral with and extending away from the first cylindrical body; the female receptacle comprising a conduit and first teeth extending outward from a section of the wall of the conduit, wherein the first teeth circumscribe three hundred and sixty degrees of the section and the conduit extends longitudinally through the female receptacle and the first cylindrical body; iii) a first end of a first expandable mesh connected to the first cylindrical body; the first expandable mesh extending away from the conduit; and iv) a first rigid curved tip connected to the second end of the first expandable mesh; the second end of the first expandable mesh opposite from the first end of the first expandable mesh; and b) a second device comprising: i) a second cylindrical body; ii) a male fitting integral with the second cylindrical body; the male fitting comprising a cylindrical channel and second teeth extending outward from an outward segment of the male fitting, wherein the second teeth circumscribe three hundred and sixty degrees of the outward segment and the cylindrical channel extends longitudinally through the male fitting and the second cylindrical body such that the first teeth and the second teeth reciprocate with each other and control lateral movements of the first and second devices; iii) a first end of a second expandable mesh connected to the second cylindrical body; the second expandable mesh extending away from the second cylindrical body in a direction opposite the first expandable mesh; and iv) a second rigid curved tip connected to the second end of the second expandable mesh; the second end of the second expandable mesh opposite the first expandable mesh, wherein the first expandable mesh, the second expandable mesh, the cylindrical channel and the conduit are aligned along a common longitudinal axis such that at least a portion of each expandable mesh engages a cavity receiving the combination.

Still another aspect of the present invention is to provide a system of interlockers securing fractured ends of a broken bone; the system comprising: a) a first interlocker comprising: i) a female receptacle comprising a conduit extending longitudinally through the female receptacle and first teeth extending from a section of a wall of the conduit, wherein the first teeth circumscribe three hundred and sixty degrees of the section; ii) a first end of a first expandable mesh connected to a first end of the first interlocker; the first expandable mesh extending away from the conduit; and iii) a first rigid curved tip connected to the second end of the first expandable mesh opposite from the first end of the first expandable mesh; and b) a second interlocker comprising: i) a male fitting comprising a cylindrical channel extending longitudinally through the male fitting and second teeth extending outward from an outward segment of the male fitting, wherein the second teeth circumscribe three hundred and sixty degrees of the outward segment and the first teeth and the second teeth reciprocate with each other and control lateral movements of the first and second interlockers; ii) a first end of a second expandable mesh connected to the second interlocker; and iii) second rigid curved tip connected to the second end of the second expandable mesh; the second rigid curved tip opposite the first rigid curved tip, wherein the first expandable mesh, the second expandable mesh, the cylindrical channel and the conduit are aligned along a common longitudinal axis and at least a portion of each expandable mesh engages a cavity receiving the system.

It is still another aspect of the present invention to provide an implant securing fractured ends of a broken bone; the implant comprising: a) a female component comprising: a conduit extending longitudinally through the female component and first teeth extending from a section of a wall of the conduit; a first end of a first expandable mesh connected to a first end of the female component and extending away from the conduit; and a first rigid curved tip connected to the second end of the first expandable mesh; and b) a male component comprising: a male fitting comprising a cylindrical channel extending longitudinally through the male fitting and second teeth extending outward from an outward segment of the male fitting; a first end of a second expandable mesh connected to the male component; and a second rigid curved tip connected to the second end of the second expandable mesh opposite the first rigid curved tip, wherein first teeth and the second teeth are interlocked to limit lateral movements of the female and male components and the first expandable mesh, the second expandable mesh, the cylindrical channel and the conduit are aligned along a common longitudinal axis such that at least a portion of each mesh engages a cavity receiving the implant.

Yet still another aspect of the present invention is to provide an implant securing fractured ends of a broken bone; the implant comprising: a) a female component receiving a corresponding male component, wherein the female and male components are aligned about the longitudinal axis of the implant; b) a first expandable mesh attached to the female component and extending along the longitudinal axis; the first expandable mesh comprising a first rigid curved tip opposed from the first expandable mesh's connection to the female component; and c) a second expandable mesh attached to the male component and extending along the longitudinal axis; the second expandable mesh comprising a second rigid curved tip opposed from the first rigid curved tip, wherein a common duct surrounds the longitudinal axis and extends from about the first rigid curved tip to about the second rigid curved tip.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 2 is a lateral cross-section of a preferred embodiment of the current combination along longitudinal axis A-A.

FIG. 3 is a perspective of a preferred embodiment of interlocked first device (30) and second device (60) of the current implant.

DESCRIPTION OF THE PREFERRED EMBODIMENTS

Figure 1:
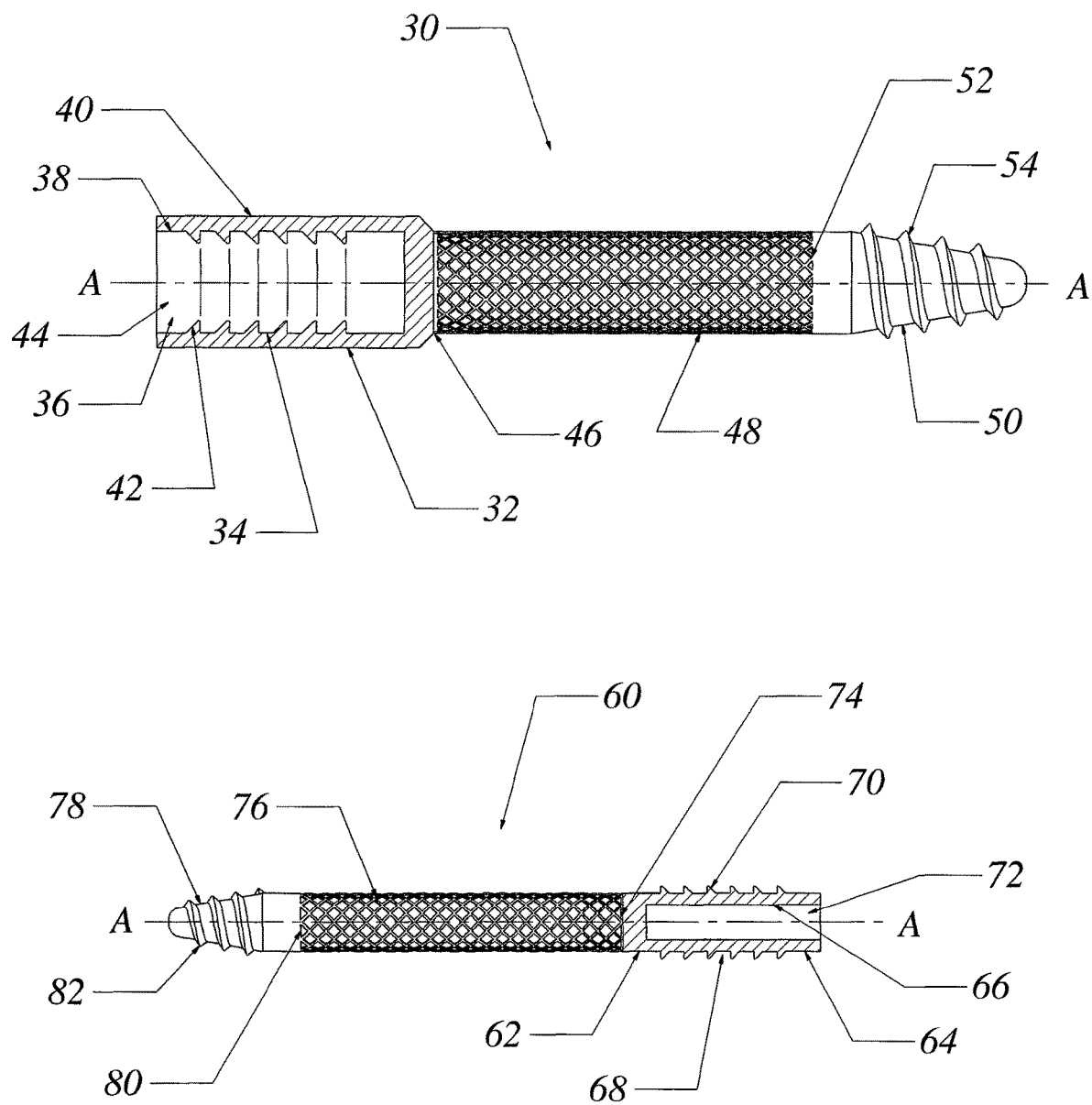
FIG. 1 shows lateral perspectives of first device (30) and second device (60) of the current system.

Although the disclosure hereof is detailed to enable those skilled in the art to practice the invention, the embodiments published herein merely exemplify the present invention.

In the most general sense, the present invention is a biocompatible system, combination or implant adapted for insertion into opposed cavities of first and second sides of a fractured bone. For some preferred embodiments of the current invention, after implantation, some portions of the implant contact the cortex of healthy (uninjured) bone. The current invention can be particularly useful for the treatment of fractured mammalian long bones.

In the practice of the current system, a guide wire is introduced to the fracture site. Thereafter, the system's implant or combination is introduced to the fracture site and the guidewire removed. A first mesh is placed inside a first side of fractured bone and a second mesh is placed inside a second side of fractured bone. One or more catheters can be inserted into the duct of the implant and be extended into the opposed meshes of the combination. In select preferred embodiments, a balloon can be utilized to expand one or both of the expandable meshes against the walls of the cavities of the first and second sides of the fracture. Adhesives, such as polymethymethacrylate or bone cement/bone augmentation material, such as Cortoss®, can be injected through the mesh to interdigitate with cortical and cancellous bone.

Unlike prior surgical methods that use forces external to the first outward side and second outward side of the fractured bone to align the first and second sides of the fractured bone, the current implant allows the combination of the interlocked male and female devices to apply internal forces to the inner cavities of the first and second fractured sides to realign the first and second fractured sides. In a preferred practice of the current system, it is anticipated that the surgeon will align the distal side by expanding the distal device's expandable mesh and applying force to the distal side's inner cavity to pull and align the distal side with the proximal side of the fracture. When adequate reduction has occurred, the surgeon can utilize a balloon to align and expand the proximal side's expandable mesh that can apply force to the proximal side's inner cavity. During surgery, the current implant can be used to align the first and second sides of the fractured bone and subsequent to surgery the implanted combination allows for dynamic compression of the aligned and proximal first and second sides of the fractured bone.

Among other things, the current combination or implant includes interlocking male and female devices or components. The male device is provided with a body and a channel and the female component is provided with a body and a conduit. Each interlocking component can also be supplied with an opening there through.

Expandable meshes extend from the interlocking bodies of the system, and the meshes can be provided with rigid tips. The rigid tips can be provided with a connector, such as a thread, for reciprocating with a surgical tool. The mesh is adapted for expansion and contact of at least a portion of the walls that surround the opposed cavities of the first and second sides of the fracture. Anatomic realignment of opposed sides of the fracture is currently understood to promote healing of the fracture, and it is believed that the closeness and precision that can be provided by the current system's anatomic realignment of the first and second sides of the fracture further improves healing of the fracture. The present invention's expandable meshes are compatible with bone cavities of differing diameters, and the current implant can provide better control of postoperative horizontal, lateral and rotational movements of the compressed first and second sides of fractured bone than prior surgical methods.

In select preferred embodiments of the current system, the channel, the conduit and the openings of the first and second bodies create a continuous duct extending along a common longitudinal axis of the combination or implant. The duct can extend from about the first tip of the first mesh to the about the second tip of the second mesh. In select preferred embodiments of the current system, the duct is created by the channel, conduit and one or more meshes. The system's duct can transport: tissue away from the injury and or irrigation to and away from the injury. The implant's duct can also be used transport biocompatible devices/substances, such as adhesives, cameras, cannulas, catheter, fiber optics, implants other than the current invention, osteogenics, pharmaceuticals, etc.

Along with stabilizing fractures, the current implant can be adapted for use to prophylactically treat weakened but unbroken bones, e.g., cancer, osteoporosis and non-unions platelets. After implantation, the present combination can also be used to transport adhesives, biopsies, chemotherapy, iliac crest marrow, parathyroid hormone, etc.

Preferred embodiments of the present invention are manufactured of titanium alloys, stainless steel, non-resorbable polymers or any other composition acceptable in the art. Within the scope of the present invention, it has advantageously been discovered that female body can have a length of from about one centimeter to about thirty centimeters and a diameter of from about two millimeters to about twenty millimeters. The male body can have a length of from about one centimeter to about thirty centimeters and a diameter of from about two millimeters to about twenty millimeters. Meshes of the current invention can have a length of from about one-half centimeter to about twenty-five centimeters and can be expanded from about two and one-half millimeters to about three centimeters. Tips of the current combination can have a diameter of from about one and one-half millimeter to about ten millimeters and a length of from about three millimeters to about twenty millimeters.

FIG. 1 shows lateral perspectives of first device (30) and second device (60) of the current system, implant, or combination.

First device (30) is provided with first cylindrical body (32). Extending away in a first direction away from first cylindrical body (32) is female receptacle (34). In select preferred embodiments, first cylindrical body (32) and female receptacle (34) are integrally formed. Female receptacle (34) is provided with conduit (36), inward wall (38), section (40) of inward waif (38) that includes teeth (42) and opening (44) opposite from the first cylindrical body (32). As shown, teeth (42) circumscribe three hundred and sixty degrees about section (40), but in other preferred embodiments, teeth (42) can be positioned about one or more divisions of section (40). Conduit (36) extends longitudinally through female receptacle (34) and first cylindrical body (32).

First end (46) of first expandable mesh (48) is connected to first cylindrical body (32). First expandable mesh (48) extends away from first cylindrical body (32) in a second direction. First rigid tip (50) is connected to the second end (52) of first expandable mesh (48). Select preferred embodiments of first rigid tip (50) are provided with threads (54) capable of interconnecting with a surgical tool (not shown).

Second device (60) is provided with second cylindrical body (62). Extending away in a first direction away from second cylindrical body (62) is male fitting (64). In select preferred embodiments, second cylindrical body (62) and male fitting (64) are integrally formed. Male fitting (64) is provided with a cylindrical channel (66), outward segment (68) that includes teeth (70) and opening (72) opposite from the second cylindrical body (62). As shown, teeth (70) circumscribe three hundred and sixty degrees about outward segment (68), but in other preferred embodiments, teeth (70) can be positioned about one or more divisions of outward segment (68). Cylindrical channel (66) extends longitudinally through male fitting (64) and second cylindrical body (62).

First end (74) of second expandable mesh (76) is connected to second cylindrical body (62). Second expandable mesh (76) extends away from second cylindrical body (62) in a second direction. Second rigid tip (78) is connected to the second end (80) of second expandable mesh (76). Select preferred embodiments of second rigid tip (78) are provided with threads (82) capable of interconnecting with a surgical tool (not shown).

FIG. 2 is a lateral perspective of the current invention's interlocked first device (30) and second device (60) showing first and second devices (30, 60) interlocked along common axis A-A of the implant, system or combination. As shown, teeth (42) of first device (30) are adapted to interlock with second teeth (70) of second device (60). The interlocking of first device (30) and second device (60) form the implant or system that can be implanted into a cavity of a bone. First expandable mesh (48) and second expandable mesh (76) can be expanded to engage the cavity. After insertion into the cavity, first expandable mesh (48), second expandable mesh (76), cylindrical channel (66) and conduit (36) are aligned along a common longitudinal axis of the implant.

FIG. 3 is a perspective of a preferred embodiment of interlocked first device (30) and second device (60) of the current implant.

Figure 4:
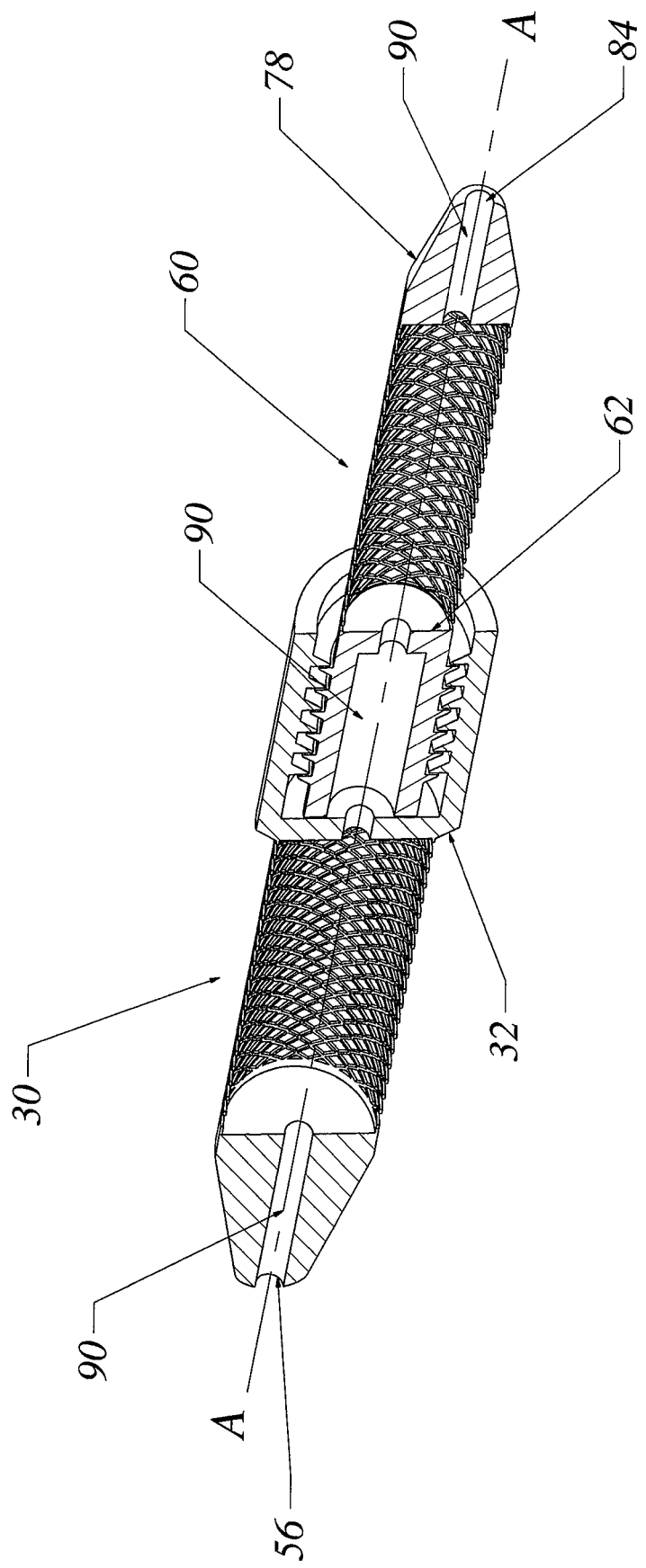
FIG. 4 is a perspective showing the duct (90) surrounding common axis A-A, where the duct (90) extends through first device (30) and second device (60).

FIG. 4 is a perspective showing duct (90) extending through first device (30) and second device (60). As shown, portions of first cylindrical body (32), second cylindrical body (62), first rigid tip (50) and second rigid tip (78) are cut away. In the preferred embodiment shown in FIG. 4, first rigid tip (50) is provided with aperture (56) and second rigid tip (78) is provided with aperture (84). Apertures (56, 84) allow ingress and egress or instruments, compositions, etc. to duct (90).

Figure 5:
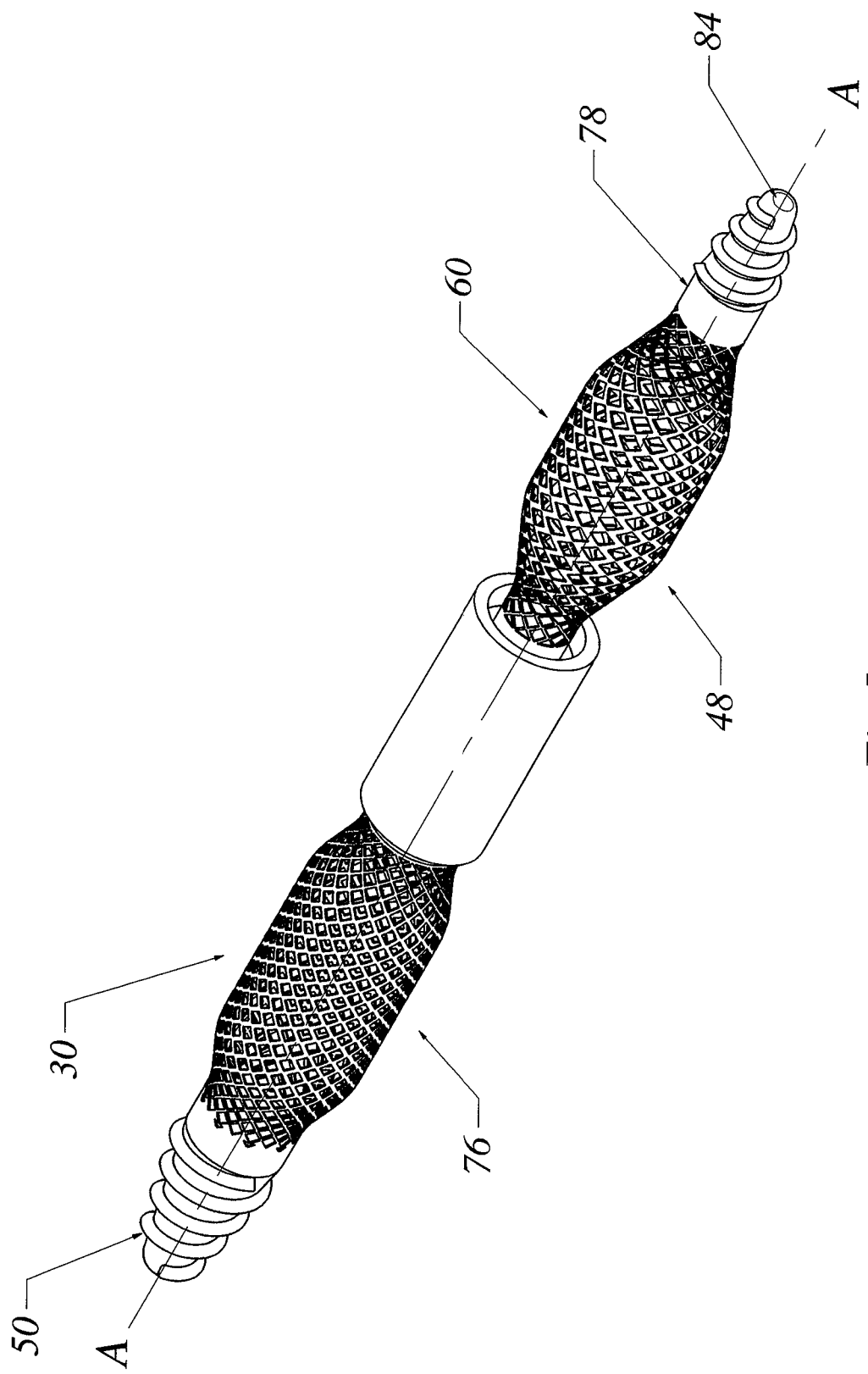
FIG. 5 is a perspective of the current implant with meshes (48, 76) expanded.

FIG. 5 is a perspective of the current implant with meshes (48, 76) expanded.

Figure 6:
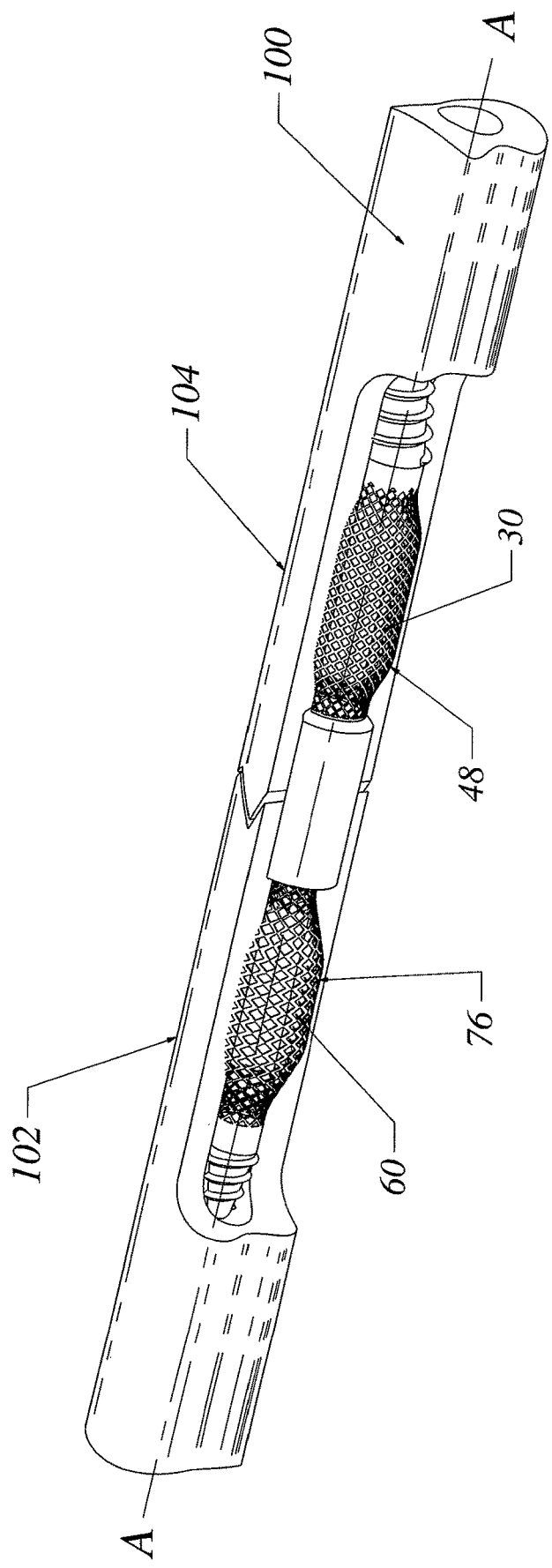
FIG. 6 is a perspective of the current combination implanted into opposed sides of a fractured bone.

With part of the fractured bone (100) cut away, FIG. 6 is a perspective of the current system implanted into opposed sides (102, 104) of the fractured bone (100). As shown, meshes (48, 76) of the current system are implanted and expanded to engage at least a portion of the wall of an inner cavity, such as the cortex, of bone (100).

It is the novel and unique interaction of these simple elements which creates the apparatus within the ambit of the present invention. Pursuant to the Article 33 of the Patent Cooperation Treaty, descriptions of preferred embodiments follow. However, it is to be understood that the best mode descriptions do not limit the scope of the present invention.

What is claimed is:

1. A combination for securing fractured ends of a broken bone; the combination comprising:
 a) a first device comprising:
  i) a first cylindrical body;
  ii) a female receptacle integral with and extending away from the first cylindrical body; the female receptacle comprising a conduit and first teeth extending inward from a section of a wall of the conduit, wherein the first teeth circumscribe three hundred and sixty degrees of the section and the conduit extends longitudinally through the female receptacle and the first cylindrical body;
  iii) a first end of a first expandable mesh connected to the first cylindrical body; the first expandable mesh extending away from the conduit; and
  iv) a first rigid curved tip connected to a second end of the first expandable mesh; the second end of the first expandable mesh opposite from the first end of the first expandable mesh; and
 b) a second device comprising:
  i) a second cylindrical body;
  ii) a male fitting integral with the second cylindrical body; the male fitting comprising a cylindrical channel and second teeth extending outward from an outward segment of the male fitting, wherein the second teeth circumscribe three hundred and sixty degrees of the outward segment and the cylindrical channel extends longitudinally through the male fitting and the second cylindrical body;
  iii) a first end of a second expandable mesh connected to the second cylindrical body; the second expandable mesh extending away from the second cylindrical body in a direction opposite the first expandable mesh; and
  iv) a second rigid curved tip connected to a second end of the second expandable mesh; the second end of the second expandable mesh opposite the first expandable mesh, wherein the first expandable mesh, the second expandable mesh, the cylindrical channel and the conduit are aligned along a common longitudinal axis and at least a portion of each expandable mesh for engaging a cavity receiving the combination, and wherein first teeth of the first device and second teeth of the second device reciprocate with each other and assist in controlling longitudinal movements of the first and second devices.

2. The combination of claim 1, wherein interlocked first device and second device create a duct.

3. The combination of claim 2, wherein:
 a) the first rigid curved tip comprises threads; and
 b) the second rigid curved tip comprises threads.

4. A system of interlockers for securing fractured ends of a broken bone; the system comprising:
 a) a first interlocker comprising:
  i) a female receptacle comprising a conduit extending longitudinally through the female receptacle and first teeth extending inward from a section of a wall of the conduit, wherein the first teeth circumscribe three hundred and sixty degrees of the section;
  ii) a first end of a first expandable mesh connected to the first interlocker; the first expandable mesh extending away from the conduit; and
  iii) a first rigid curved tip connected to a second end of the first expandable mesh opposite from the first end of the first expandable mesh; and
 b) a second interlocker comprising:
  i) a male fitting comprising a cylindrical channel extending longitudinally through the male fitting and second teeth extending outward from an outward segment of the male fitting;
  ii) a first end of a second expandable mesh connected to the second interlocker; and
  iii) a second rigid curved tip connected to a second end of the second expandable mesh; the second rigid curved tip opposite the first rigid curved tip, wherein the first expandable mesh, the second expandable mesh, the cylindrical channel and the conduit are aligned along a common longitudinal axis and at least a portion of each expandable mesh for engaging a cavity receiving the system, and wherein first teeth of first device and second teeth of second device reciprocate with each other and assist in controlling longitudinal movements of the first and second interlockers.

5. The system of claim 4, wherein:
 a) the first rigid curved tip comprises threads; and
 b) the second rigid curved tip comprises threads.

6. The system of claim 5 wherein the first interlocker and the second interlocker create a duct.

7. The system of claim 6, wherein:
 a) the first interlocker comprises a first cylindrical body; or
 b) the second interlocker comprises a second cylindrical body; or
 c) the first interlocker comprises a first cylindrical body and the second interlocker comprises a second cylindrical body.

8. An implant for securing fractured ends of a broken bone; the implant comprising:
   a) a female component comprising: a conduit extending longitudinally through the female component; first teeth extending from a section of a wall of the conduit; a first end of a first expandable mesh connected to a first end of the female component and extending away from the conduit; and a first rigid tip connected to a second end of the first expandable mesh; and
   b) a male component comprising a cylindrical channel extending longitudinally through the male component; second teeth extending outward from an outward segment of the male component; a first end of a second expandable mesh connected to the male component; and a second rigid tip connected to a second end of the second expandable mesh opposite the first rigid tip, wherein the first expandable mesh, the second expandable mesh, the cylindrical channel and the conduit are aligned along a common longitudinal axis and at least a portion of each expandable mesh for engaging a cavity receiving the implant.

9. The implant of claim 8 wherein the female component and the male component create a duct.

10. The implant of claim 9, wherein first teeth of female component and second teeth of male component reciprocate with each other and assist in controlling longitudinal movements of the female component and the male component.

11. The implant of claim 10, wherein:
   a) the first rigid tip comprises threads; and
   b) the second rigid tip comprises threads.

12. The implant of claim 11, wherein either the first teeth circumscribe three hundred and sixty degrees of section of the female component or second teeth circumscribe three hundred and sixty degrees of the outward segment of the male component.

13. The implant of claim 12, wherein:
   a) first rigid tip comprises a curve; and
   b) second rigid tip comprises a curve.

14. An implant for securing fractured ends of a broken bone; the implant comprising:
   a) a first expandable mesh attached to a female component comprising first teeth extending from a section of a wall of a conduit; the first expandable mesh comprising a first rigid tip opposite from the first expandable mesh's connection to the female component;
   b) a second expandable mesh attached to a male component comprising second teeth extending outward from an outward segment of the male component adapted to interlock with the first teeth; the second expandable mesh comprising a second rigid tip opposite from the second expandable mesh's connection to the male component; and
   c) a common duct created by joining the female component and corresponding male component.

15. The implant of claim 14, wherein the common duct surrounds the implant's longitudinal axis and extends from about the first rigid tip to about the second rigid tip and at least a portion of the first expandable mesh, the first rigid tip, the second expandable mesh and the second rigid tip for engaging a cavity receiving the implant.

16. The implant of claim 15, wherein first teeth of female component and second teeth of male component reciprocate with each other and assist in controlling longitudinal movements of the female component and the male component.

17. The implant of claim 16, wherein:
   a) the first rigid tip comprises threads; and
   b) the second rigid tip comprises threads.

18. The implant of claim 17, wherein either the first teeth circumscribe three hundred and sixty degrees of section of the female component or second teeth circumscribe three hundred and sixty degrees of the outward segment of the male component.

19. The implant of claim 18, wherein:
   a) the first rigid tip comprises a curve; and
   b) the second rigid tip) comprises a curve.

* * * * *